(12) United States Patent
Bozsik et al.

(10) Patent No.: US 6,689,577 B1
(45) Date of Patent: Feb. 10, 2004

(54) REAGENT AND PROCEDURE FOR THE DETECTION OF PATHOGENS, ESPECIALLY SPIROCHETES FROM BODY FLUIDS

(75) Inventors: Bela Pal Bozsik, Budapest (HU); Janos Albert, Budapest (HU); Ilona Dufla, Budapest (HU)

(73) Assignee: Bela P. Bozsik, Budapest (HU)

(*) Notice: Subject to any disclaimer, the term of this patent is extended or adjusted under 35 U.S.C. 154(b) by 0 days.

(21) Appl. No.: 09/913,572

(22) PCT Filed: Feb. 16, 2000

(86) PCT No.: PCT/HU00/00013

§ 371 (c)(1),
(2), (4) Date: Jan. 2, 2002

(87) PCT Pub. No.: WO00/49405

PCT Pub. Date: Aug. 24, 2000

(30) Foreign Application Priority Data

Feb. 17, 1999 (HU) .............................. 9900414

(51) Int. Cl.$^7$ ................................. C12Q 1/02
(52) U.S. Cl. .............................. 435/29; 435/29; 435/30; 435/31; 435/32; 435/8
(58) Field of Search ............................ 435/30, 32, 40.5, 435/8

(56) References Cited

PUBLICATIONS

Hulinska et al., "Electron microscopy and the polymerase chain reaction of spirochetes from the blood of patients with Lym disease", Cent Eur J Public Health, Dec. 1993, 1(2):81–5.*

Dorwood et al., "Immune capture and detection of Borrelia burgdorfi antigens in urine, blood, or tissues from infected ticks, mice, dogs, and humans", J Clin Microbiol, Jun. 1991, 29(6):1162–70.*

Sciotto et al., "Detection of Borrelia in acridine orange–stained blood smears by fluorescence microscopy", Arch Pathol Lab Med, Jul. 1983, 107(7):384–6.*

* cited by examiner

Primary Examiner—Leon B Lankford, Jr.
Assistant Examiner—R Davis
(74) Attorney, Agent, or Firm—Duane Morris LLP (57) ABSTRACT

A reagent for microscopy-based detection of pathogens, especially spirochetes, from body fluids characterized by that containing the following ingredients: tetracain (125–200 mg/l), mannit (1500–2000 mg/l), EGTA (etilene bis[oxyetiline-nitrilo]-tetraacetate), 0.76–0.114 mg/l magnesium-chloride (preferably in amount of 0.10 mg/l), caffeine-sodium-benzoate (2000–4000 mg/l), glucose (1800–2200 mg/l), glycerol (75–105 mg/l), optimally tri-sodium-citrate (preferable in an amount of 10000 mg/l), Hoechst 33342 dye (1.11 mg/l), if required 20 to 40 ml of distilled water and RPMI 1640 culture media to make 100 ml. Also, a method for detecting pathogens.

15 Claims, 5 Drawing Sheets

INDIRECT IMMUNOFLUORESCENT ASSAYS
USING SPECIFIC MONOCLONAL ANTIBODIES PROVE
THAT THE SPIROCHETOID BODIES ARE IDENTICAL TO
*BORRELIA BURGDORFERI SENSU LATO*.

- Indirect Immunofluorescent assay using specific antibodies (anti-OspA) shows two *Borrelia burgdorferi sensu lato(A)* organisms joined in a characteristic V-shape*(B)*. The original magnification is 60 times.
- Different types of shedding can be seen at the same time, which proves that the vital signs of the Spirochetoid bodies *(i.e. B.burgd.s.l.)* are not affected by our reagent.
- Peripheral shedding*(C)* previously described in culture by professor Barbour who kindly donated monoclonals binding to OspA and Flagellin. This is the first demonstration of the shedding in preparation of human blood.
- Central shedding*(D)* This is the First Demonstration(Human Blood). The bilayer structure of flagellin gives possibility for the shedding to became into existence.

Fig.1.

SHEDDING IS A VITAL SIGN OF *BORRELIA BURGDORFERI SENSU LATO*.
IT PRODUCES MACROMOLECULAR IMMUNOCOMPLEXES, HIDING ANTIBODY MOLECULES AND
MASKING THEM DURING DETERMINATION, FURTHER ON BRINGING AUTOIMMUNITY.
IT ALSO PROVES THE NATURAL ENVIRONMENT IN OUR REAGENT

THIS PICTURE IS KINDLY DEDICATED TO COLLEAGUES, ESPECIALLY TO
LAVOIE, GARON, SCHUTZER, COYLE IN THE US, ABERER, CEVENINI AND MIKLÓSSY IN EUROPE

THE DIFFERENTIAL DIAGNOSIS OF SPIROCHETOSES

| NAME OF ILLNESS / PATHOGEN<br>CHARACTERISTICS | LYME BORRELIOSIS<br>Borrelia burgdorferi sensu lato | FEBRIS RECURRENS<br>Borrelia recurrentis | LUES<br>Treponema pallidum | LEPTOSPIROSIS<br>Leptospira Interrogans |
|---|---|---|---|---|
| Zoonosis | + | +/- | - | +/- |
| Source of Infection | Ticks | Lice (Europe) Ticks (NORTH AND SOUTH AMERICA) | Sexual Intercourse | Rats, Dogs |
| Transmitted in | saliva, gastric juice of ticks | saliva and body fluids of vectors | body fluids | urine, tissues |
| Means of Transmission | blood-sucking | blood-sucking | epithelial injury | contaminated water |
| Incubation Period | 2-40 days | 7 days | 10-90 days | 2-20 days |
| Onset | Insidious | Abrupt | Gradual | Variable/Abrupt |
| Waxing and Weaning of Symptoms | typical | typical | - | - |
| Fever | Subfebricity | Recurrent High Fever | Subfebricity | High |
| Rashes | Lyme-rash (ECM) | rash | chancre-rash-gumma | rash |
| Hepatosplenomegaly | - | + | - | +/- |
| Icterus | +/- | + | - | + |
| Lymph Node Involvement | - | + | + | +/- |
| Bleeding / Bleeding diathesis | - | - | - | + |
| Pyelonephritis | - | - | +/- | + |
| Arthritis | + | - | +/- | - |
| Diameter of Pathogen (μm) | 0,1-0,3 | 0,5-1,0 | 0,1-0,3 | 0,1-0,3 |
| – Length (μm) | 7,0-30,0 | 20,0-60,0 | 6,0-15,0 | 5,0-18,0 |
| – Characteristic Tail | - | - | - | + |
| – Antigen Shifts | + | + | - | - |
| – Metabolism | Semi-anaerobic | Anaerobic | Anaerobic | Aerobic |
| – Anilin-stainable | +/- | + | - | - |
| – Cultivation | difficult | + | - | + |
| Effectivity of Antibiotics | + | + | + | +/- (Questionable after day 4) |
| Duration of Treatment | 6-12 weeks | 1,5 weeks | 8-10 days/2x4 weeks | 1 week |
| Frequency of Relapses | Frequent | - | Occasional | Occasional |

Fig. 5.

ured for the Recovery of *Borre-*
REAGENT AND PROCEDURE FOR THE DETECTION OF PATHOGENS, ESPECIALLY SPIROCHETES FROM BODY FLUIDS This application claims priority of the earlier filing date, under 35 U.S.C. 119, of PCT International Application No. PCT/HU00/00013, filed on Feb. 16, 2000, published in English.

BACKGROUND OF THE INVENTION

The invention is a reagent and a microscopy-based procedure for the detection of pathogens, especially spirochetes, from body fluids.

Provided that sterility is observed, the reagent according to the invention makes it possible to examine human body fluid samples under a dark-field microscope without staining.

As early as in 1683, the Dutch scientist, Anthonij van Leeuwenhoek discovered the spirochetes through his microscope and informed the British Royal Society about his discovery. Two centuries later, József Fodor was the first to discover that the blood of healthy individuals does not contain germs.

In comparison to serological and PCR techniques, the independence of the morphological examination (microscopy) of antigenicity and other changes (which—among spirochetes—is most typical of Borreliae) as well as of the emergence of new subspecies is still considered an advantage. The genetic make-up and the phenotype of these pathogens can even change during the illness of a single person, and some of these changes may not be detectable using the current techniques. After excluding infections with incompatible clinical presentations and higher local probabilities, morphological identification of the causative agent is diagnostic.

Despite the fact that the existence of spirilla was unequivocally demonstrated with the use of the microscope, even the well-known and widely recognized studies of Leeuwenhoek were forgotten—only to be re-discovered centuries later.

Indeed, conventional staining can hardly make these extremely thin and long pathogens visible; the tedious and most sophisticated technique of silver impregnation is still the only way to detect them in smears and slides. Cultivation is still problematic.

Since 1909, however, dark-field microscopy has made it possible to firmly diagnose spirochetoses from native, not fixed slides before the appearance of antibodies, provided the samples are taken from a patient who shows certain well-defined symptoms.

This means that the diagnosis can be made at an early stage, when treatment is expected to be most effective.

It was microscopy that proved that from the portal of entry, pathogens reach all organs (including the CNS) via the bloodstream and the lymphatic system.

The laboratory diagnosis of borrelioses with different clinical presentations is based primarily on the detection of spirochetes from blood samples. This is easily accomplished in recurrent fever because normally, there is a large number of *B. recurrentis* present. Besides, other morphological properties of this pathogen (shown in the table enclosed) and the fact that this pathogen is easy to stain also make its detection easier. There are mild cases, however, when the symptoms suggest the diagnosis of recurrent fever but the cell count is too low for the conventional methods to detect the causative agent. To solve this problem, the technique of microhematocrit concentration (double centrifugation of blood samples) has been used since 1972. Microscopy is superior in that the test result is not affected by the changing antigenicity of Borreliae. [Goldsmid, J M. Mohamed: The use of Microhematrocit Technic for the Recovery of *Borrelia duttonii* from the Blood, Am. J. Clin. Pathol. 58:165–169 (1972)].

Sample concentration has also been used to enhance conventional microscopy in parasitology. This way, pathogens can be detected more efficiently.

The diagnosis of Lyme borreliosis and the identification of its causative agent emerged as a new problem.

It is known that, in the seventies there was an outbreak of arthritis cases among the children who lived around the town of Lyme, Conn., USA. Ticks were soon identified as the vectors but the causative agent of the mysterious Lyme disease was not identified until much later.

After the unsuccessful investigations using top technologies, Willy Burgdorfer discovered the causative agent with a microscope and identified it as a new spirochete. This pathogen is referred to as *Borrelia burgdorferi sensu lato* [(Burgdorfer, W, Barbour, A. G., Hayes, S., F., Benach, J. L, Grunwaldt, E., Davis, J. P: Lyme Disease—a tick-borne spirochetosis? Science, 216(4552): 1317–9, Jun. 18, 1982)].

As mentioned above, morphological examination has long been included in the laboratory diagnosis of spirochetoses. If dark-field microscopy is employed, concentrated fluid samples do not need to be stained, which means that the long and thin spirochetes are not washed off the slides, which, in turn, increases sensitivity.

Soon after the introduction of this technique, which has now been used for decades, it was noted that pseudospirochetes (also known as myeloid figures), which are formed mainly during the degradation of red blood cells, can mislead the examiner whether it is human or animal blood that is examined. These artifacts are most likely to be present when stored samples or the stomach contents of blood-sucking insects (louse or ticks) are examined for infection. This issue is addressed in the following articles:

Chamber, H.: A new spirochaeta found in human blood; Lancet 1913; 1: 1728–1729;

Brecher, G.; Bessis, M: Present status of spiculed red cells and their relationship to the discocyte, echinocyte transformation: a critical review. Blood 1972; 40: 333–344;

Smith, T F.; Wold, A D.; Fairbanks, V F.; Washington, J A 2nd; Wilkowske, C J.: Pseudospirochetes a cause of erroneous diagnoses of leptospirosis. Am. J.Clin. Pathol. 1979; 72: 459–63;

Greene,R T.; Walker,R L.; Greene,C E.: Pseudospirochetes in animal blood being cultured for *Borrelia burgdoiferi*. J.Vet. Diagn.Invest. October 1991; 3(4): 350–2;

Mursic,V P.; Wanner,G; Reinhardt,S; Wilske,B; Busch,U; Marget,W: Formation and cultivation of *Borrelia burgdorferi* spheroplast-L-form variants. Infection. 1996; 24: 218–26.

At the same time, however, *Borrelia burgdorferi sensu lato* even has several different morphological patterns in cultivation. Degenerative forms are also present if antibiotics are added to the culture (Aberer,E; Duray,P H: Morphology of *Borrelia burgdorferi*: structural patterns of cultured borreliae in relation to staining methods. J.Clin.Microbiol. 1991; 29(4): 764–72;

Barbour,A G; Todd,W J; Stoenner,H G: Action of penicillin on *Borrelia hermsii*. Antimicrob.Agents.Chemother. May; 21, 1982(5): 823–9;

Kersten,A; Potschekm,C; Rauch,S; Aberer,E: Effects of penicillin, ceftriaxone, and doxycycline on morphology of *Borrelia burgdorferi*. Antimicrob.Agenst.Chemother. 1995; 39(5): 1127–33.)

Today the diagnosis of spirochetoses is not problematic, except for borrelioses, which still present a challenge worldwide.

It is the direct identification of *Borrelia burgdorferi sensu lato* that can unambiguously verify Lyme disease. This is a tedious and ineffective process because the causative agent is difficult to cultivate and the low cell count of tissue and body fluid samples makes microscopy unworkable. Not even the newer genetic tests are sensitive enough in this case.

The indirect techniques used in the diagnosis of Lyme borreliosis are discussed below.

In this approach, host antibodies produced in response to *Borrelia burgdorferi sensu lato* infection are detected; the idea behind it is that nothing else but the infection can cause the antibody titers to rise. During the first stage of this infection, antibody production is slower than usual. Antibodies do not appear until weeks after the infection and are only rarely present throughout the whole course of the disease because titers keep changing and—after some time—they may become normal without any intervention. This makes it difficult to define the threshold titer. There is no clinically applicable threshold that could make a clear-cut distinction between those who are infected and those who are not. Besides, generation cycles of the causative agent cause a fluctuation of the early—IgM type—antibody titers. As far as we know, this is the only disease in which the causative agent blocks the production of the more specific and more effective IgG type antibodies, which normally follows the production of IgM. There are even cases of Lyme borreliosis in which only the early (IgM type) antibodies are present years after the infection.

What has been said so far affects all antibody assays. That is to say, comparative studies can only compare the sensitivity of the techniques in question.

Thus, it would be a big mistake to base the laboratory diagnosis of Lyme borreliosis on the traditional evaluation of a single test. Test results are sometimes considered non-specific in this case. The chances of non-specific reactions are known to be higher in spirochetoses but they can be avoided with traditional pre-test absorption, which removes the non-specific antibodies that could give a false reaction. If the test result is negative, physicians may doubt the validity of the patients' complaints and abandon the possibility of Lyme borreliosis even though antibody production may be inadequate or blocked, the technique employed may not be able to detect all antibodies or the threshold value may not be set correctly.

At the same, the clinical presentation may be compatible with the diagnosis but traditional techniques may not verify it.

Figure 1:
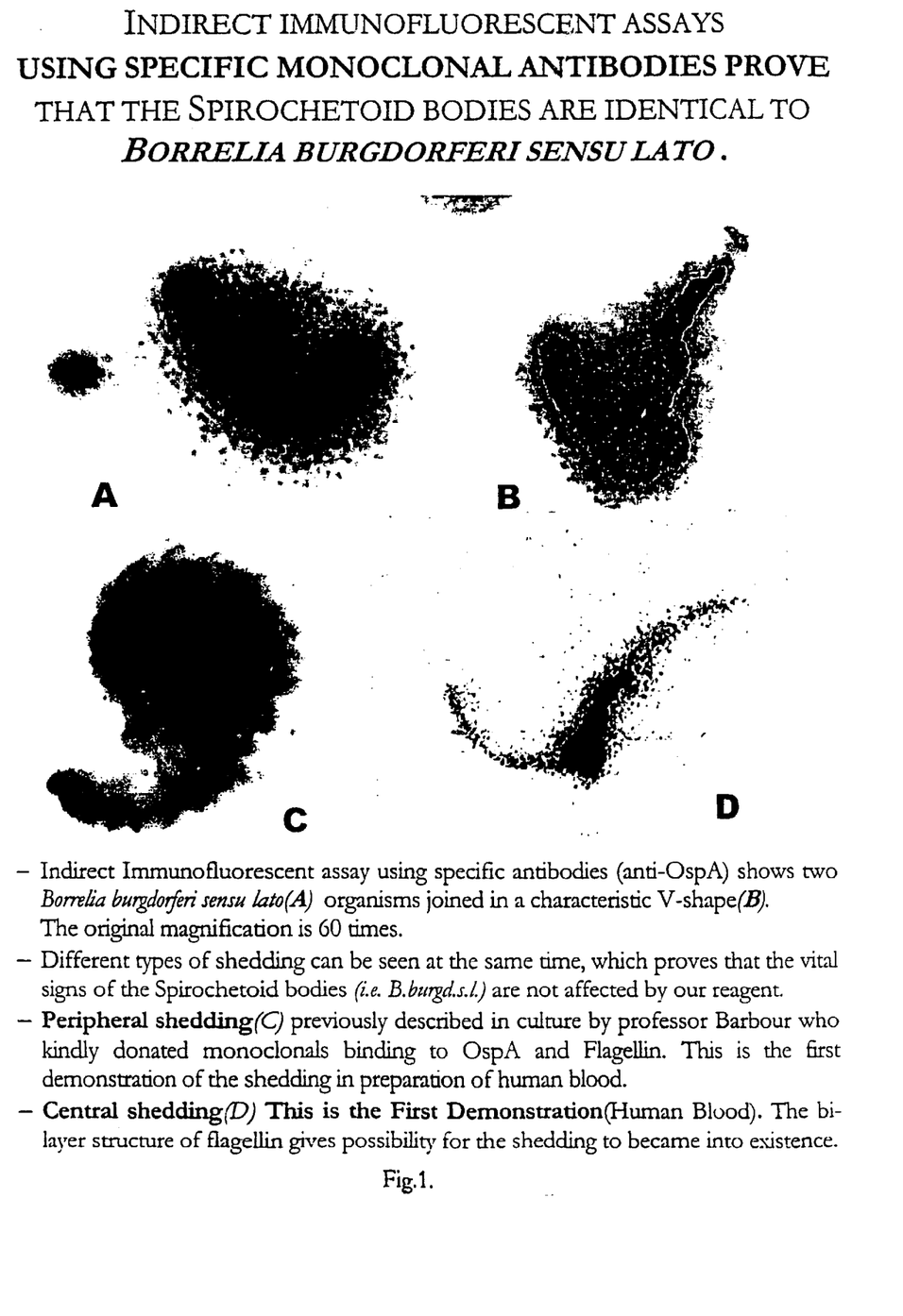
Figure 2:
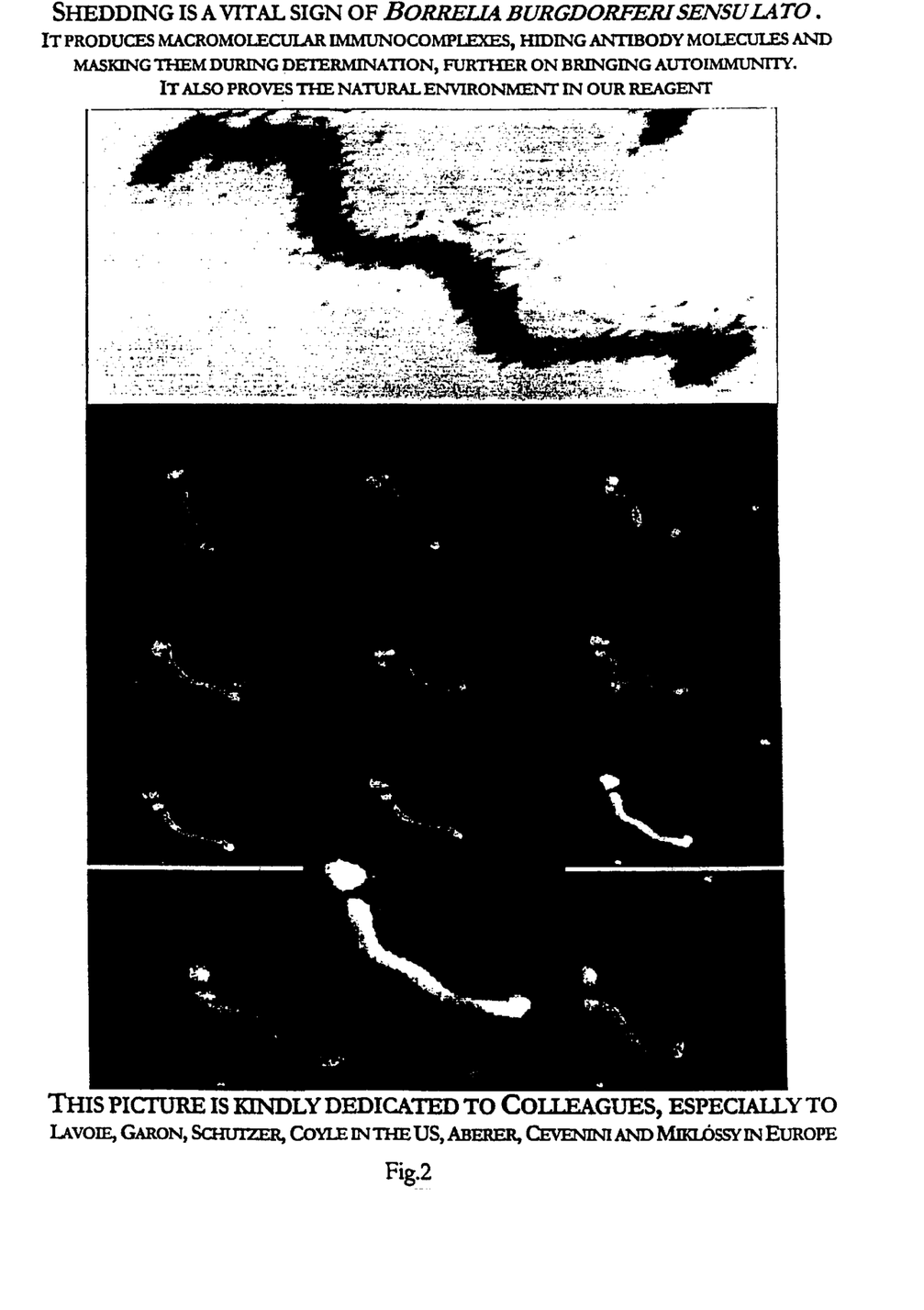
Figure 3:
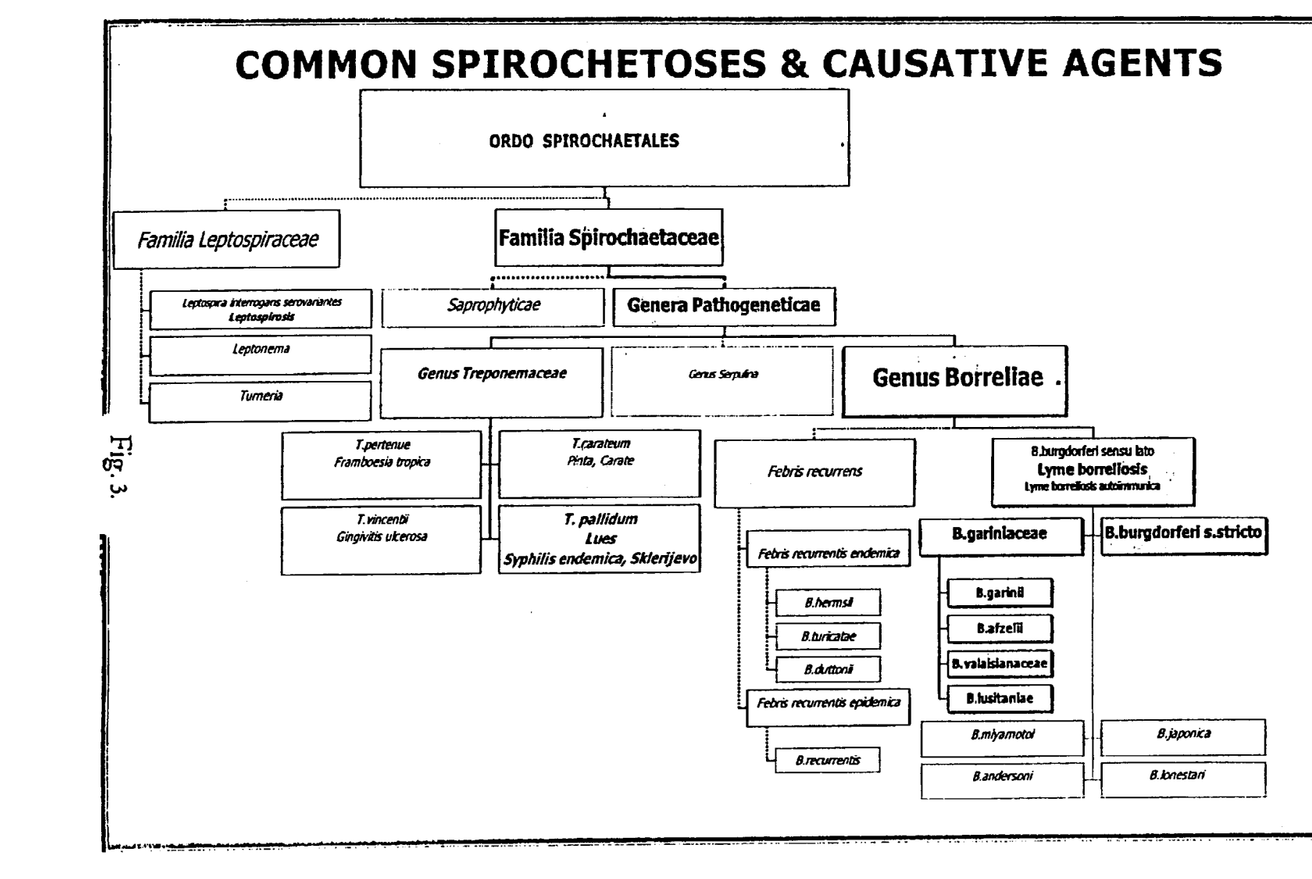
Figure 4:
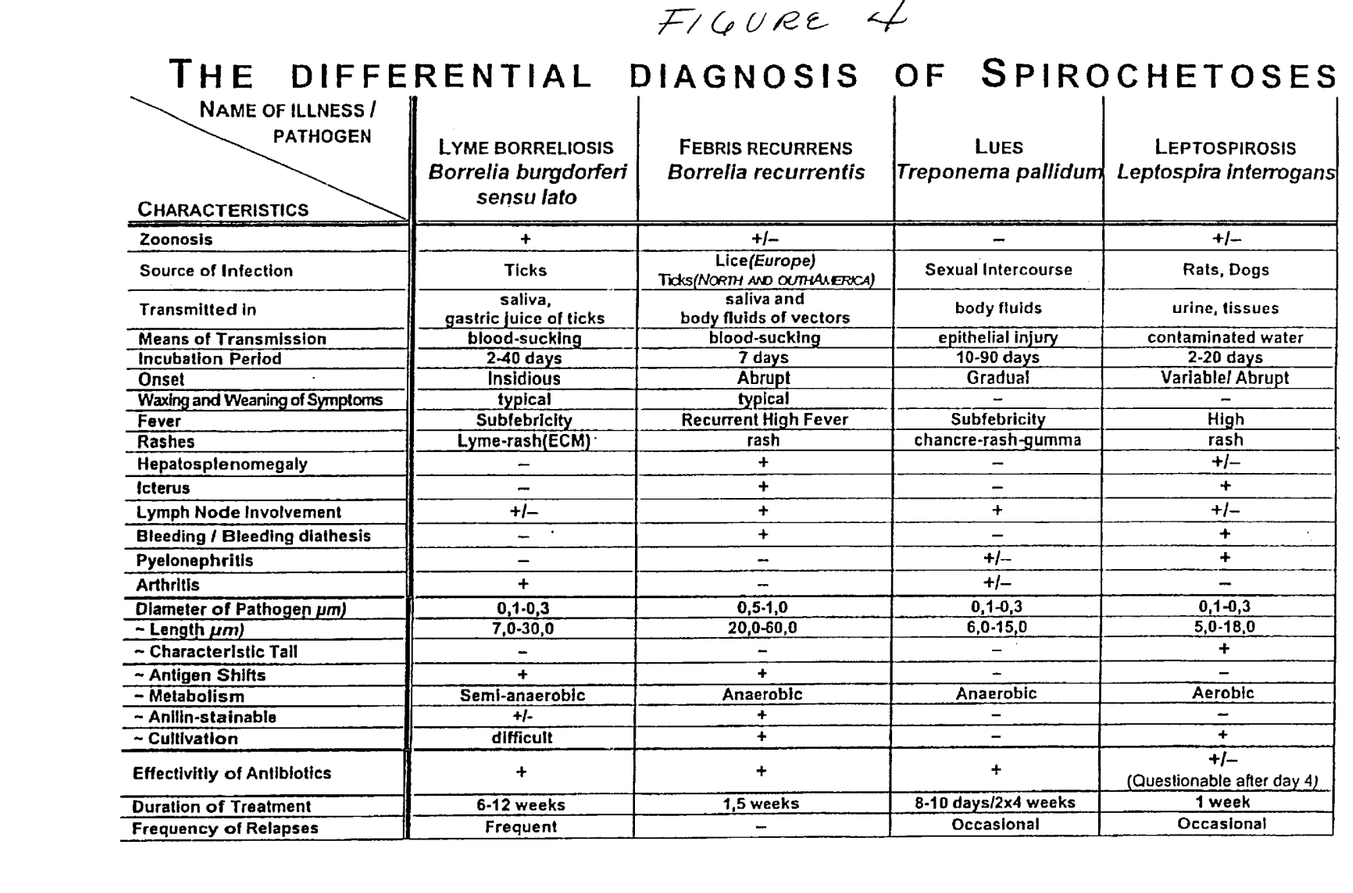
Figure 5:
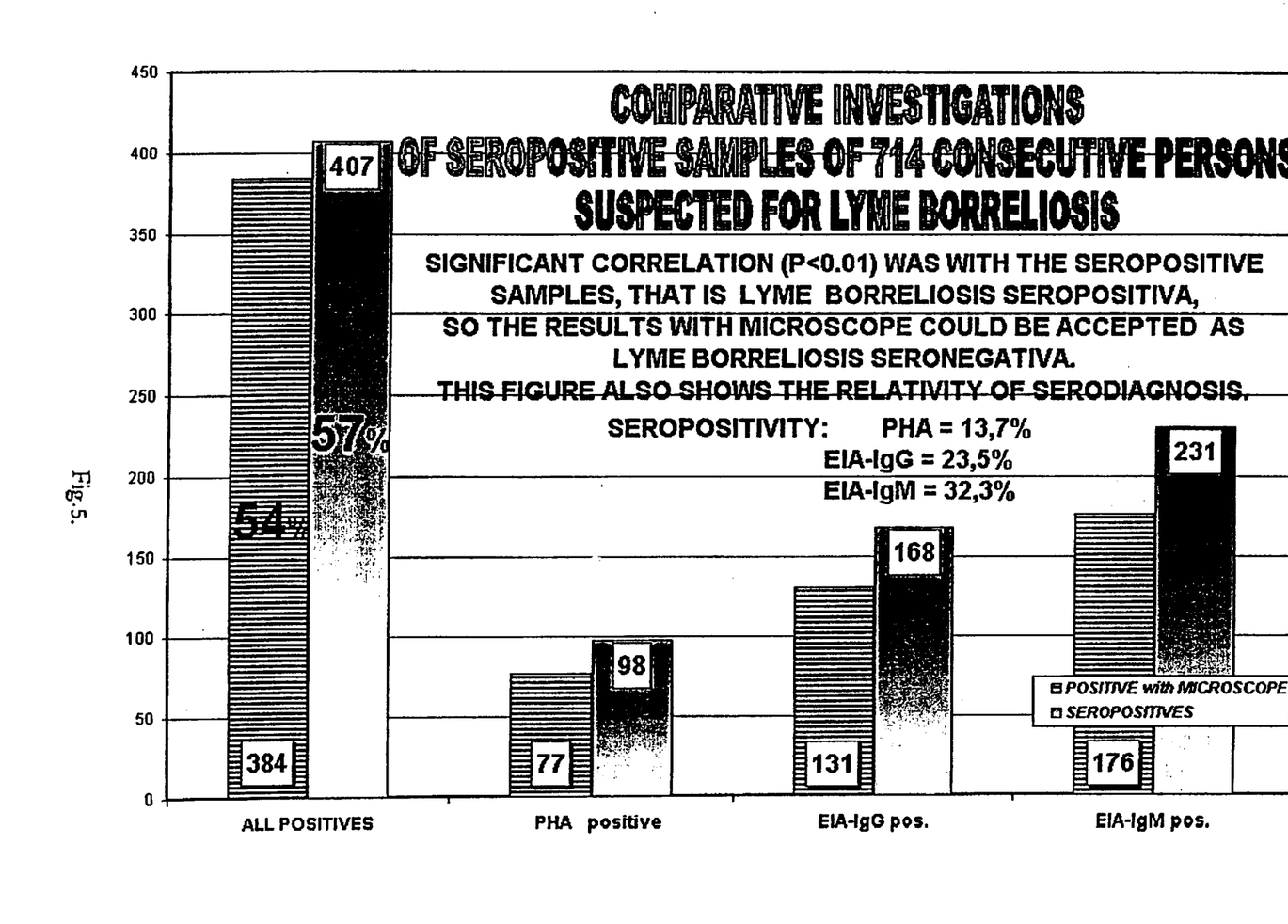

The existence of spirochetoid bodies and the assumption that they are identical with *Borrelia burgdorferi sensu lato* is indirectly verified by the fact that the prevalence of the disease that they cause is quite high world-wide and Hungary has an even higher rate of infection. The results of a comparative study shown in Table III and FIG. 1 provide indirect and direct evidence, respectively. High prevalence may be explained by the fact that despite the availability of very potent antibiotics, the treatment of this disease is still difficult. Therefore, it may well be assumed that there is a continuous accumulation of cases. Mention must be made of spontaneous healing, which is a theoretical possibility but has not been proven, since relapse may even occur after 30 years of asymptomatic disease.

As is known, both tick-borne encephalitis and Lyme borreliosis can develop after the same tick-bite. In Hungary, reliable data is available regarding the incidence of tick-borne viral encephalitis, which has been included in the national disease surveillance for almost two decades: between 200 and 400 new cases are reported each year. We know what percentage of ticks carries the bacterial and viral pathogens. The incidence of Lyme borreliosis (LB) can then be calculated as follows:

$$LB = \frac{\text{the percentage of ticks carrying the bacteria}}{\text{the percentage of ticks carrying the viruses}} * \text{the incidence of } KEC$$

The percentage of ticks carrying the viruses varies in different parts of the country but on average, 1 of 1000 ticks is infected in Hungary.

Many more ticks—at least 1 of ten—carry the bacteria, however. This is true of all of Hungary and even Europe; the causative agent of Lyme borreliosis can be detected in at least 1 of 10 ticks collected anywhere in Europe.

In short, the possibility of being infected by *Borrelia burgdorferi* is one hundred times higher than that of tick-borne viral encephalitis (KEC).

This helps us to estimate the incidence of Lyme borreliosis, the exact laboratory diagnosis of which is yet to be determined.

Based on what has been said so far, the incidence of Lyme borreliosis can be estimated as follows:

$$LB = \frac{1/10}{1/1000} * 200$$

The literature and the above formula both predict at least 20,000 new cases in Hungary each year. After tick bites, the viral and bacterial infections are expected to develop independently while the number of cases are expected to reflect the ratio of ticks carrying the two pathogens. If one also accepts the validity of the fact that only an insignificant number of Lyme borreliosis patients were treated adequately before 1990, then it might be inferred that in Hungary, as many as maybe one million people (at least 10 percent of the population today) may have become infected with Lyme borreliosis during the past sixty years.

This makes the diagnosis of Lyme borreliosis much more probable than that of other spirochetoses. Therefore, the spirochetoid bodies are most likely to be *Borrelia burgdorferi sensu lato*; this may also be a valid statement for other continents provided that the test result is viewed in the light of the clinical presentation.

Lyme borreliosis can often be diagnosed using conventional laboratory techniques and can often be cured with antibiotics. However, no reliable test to identify the seronegative cases of Lyme borreliosis (when the clinical presentation strongly suggests the diagnosis but serological techniques fail to verify the infection) has existed until now.

Lyme borreliosis reinfections are also known to occur due to the fact that—because of antigenicity changes and specific immunosuppression—host antibodies are unable to provide protection. The shedding of *Borrelia burgdorferi sensu lato* shown in Figure enclosed may also play a role in this process. Reinfection can therefore result in disease. The seronegative form of Lyme borreliosis is quite common.

In short, there is no single diagnostic technique that could verify all cases of Lyme borreliosis at present.

The aim of the invention is suppletory: to work out a technique and a reagent which is more suitable for the detection of spirochetes and can reliably verify all clinical forms of Lyme borreliosis provided that clinical symptoms are also taken into account. When used as a screening test, positive results mean that close follow-up is needed. The invented technique can eliminate the disadvantages of other techniques.

The following considerations led to the development of the invention.

In view of the state of the art in diagnostic techniques discussed above, the problem has been tried to solve by improving the microscopy-based technique. To achieve this aim it has been to make sure there is a sufficient number of pathogenic spirochetes in the samples and there are no artifacts.

As noted above, the study of the first cases of Lyme borreliosis made it clear that it is only via the circulation that *Borrelia burgdorferi sensu lato* can disseminate from the site of the tick bite and reach different organs.

In a study made at a university in Vienna, Austria in 1985, Professor Stanek and his colleagues found that in artificially infected laboratory animals bacteremia could be detected using dark-field microscopy as well as conventional microscopy after Giemsa staining: the *Borrelia burgdorferi sensu lato* injected subcutaneously appeared in the circulation and remained detectable continuously. The number of bacteria detected was changing in seven to eight day cycles. They realized that the number of pathogens is changing and that in certain periods of the generation cycle spirochetes are more difficult to detect. [(Stanek, G.; Burger, I; Hirschl, A.; Wewalka, G.; Radda, A: Borrelia transfer by ticks during their life cycle Studies on laboratory animals. Zbl. Bakt. Mikrobiol. Hyg. A., 263: 29–33: 1986)]

In a paper published in 1998, a research team that had been working unsuccessfully on the cultivation of *Borrelia burgdorferi* from blood for years described a procedure for increasing the yield of blood cultures. They used this procedure to prove the assumption that the reason for their previous failure was insufficient sample quantity rather than the lack of pathogens. [(Wormser, G P et al: Improving the Yield of Blood Cultures for Patients with Early Lyme Disease, J. Clin. Microbiol. 36:296–298, 1998)].

All this supported the theory that dark-field microscopy can be adapted to the examination of concentrated blood and other body fluid samples. However, it has been realised that until the formation of myeloid figures is prevented, dark-field microscopy couldn't be put into practice.

GENERAL DESCRIPTION OF THE INVENTION

As the title suggests, a new reagent has been developed that can slow down the aging (membrane hardening) of human erythrocytes, leukocytes, platelets and squamous epithelial cells in the samples. It has been found that the reagent according to the invention stops the amoeboid movement of leukocytes and the fragmentation of platelets. Thus, myeloid figures are not formed. The membrane of accidentally formed myeloid figures is also hardened. Consequently, they do not even exhibit Brownian movement; they simply float along. The movement and the cell division of *Borrelia burgdorferi sensu lato* remained unaffected by the invented reagent. This is how shedding could be observed, which had only been noted in cell cultures.

DETAILED DESCRIPTION OF THE INVENTION

The essential ingredients of the reagent according to the invention are the following: tetracain (125–200 mg/l), mannit (1500–2000 mg/l), EGTA (etilene-bis[oxyetiline-nitrilo]-tetraacetate) 0.76–0.114 mg/l, magnesium-chloride (preferably in an amount of 0.60 mg/l), caffeine-sodium-benzoate (2000–4000 mg/l), glucose (19000–22000 mg/l), glycerol (75–105 mg/l), tri-sodium-citrate (preferably in an amount of 10000 mg/l), Hoechst 33342 dye (1.00 mg/l,) if required 20 to 40 ml of distilled water and RPMI 1640 culture media to make 100 ml.

During the procedure according to the invention, a given amount of reagent is added to human blood or other body fluid samples. The samples are then shaken, incubated and stored, if needed, Blood cells, platelets and pathogenic bacteria are then separated from the rest of the sample, and then the remainder is concentrated and examined under a microscope.

Blood cells, platelets and pathogenic bacteria can be separated with sedimentation, slow centrifugation or filters. Concentration is accomplished with high-speed centrifugation.

It has been solved by the invention, that a simple and cheap traditional technique can be used to test human body fluid samples too. In our experience, it is still possible to detect the pathogenic bacteria if there are less than 10 bacteria in a milliliter of centrifuged native blood samples. In comparison, the threshold for the detection of Lyme borreliosis with PCR, which is currently considered the most sensitive but can only be done in specially equipped laboratories, is between 40 and 100 germs per ml; besides, as many as possible primers specific to different sub-strains should be available.

It should be noted that further morphological, immunocytological and immunoserological examination of the centrifuged sample treated with the reagent according to the invention is also possible. Furthermore, it can also be utilized for PCR and cultivation. In the latter cases, filtering is recommended before concentrating the sample.

The analysis of examination data can also provide the basis for a novel theoretical classification that reflects more aspects of the pathogenesis of Lyme borreliosis.

The technique according to the invention makes it possible to study the current state of pathogenesis and determine the activity of Lyme borreliosis in a given patient. A fast and reliable diagnosis can be made even when serological tests are negative. The reagent and the procedure according to the invention provides reliable data to aid treatment (which is still controversial), monitor treatment effects and predict relapses before the development of humoral immune response or after it has been blocked and all this is independent of autoimmune responses.

BEST MODE OF CARRYING OUT OF THE INVENTION

The following is a list of examples of the invented reagent, without restricting.

EXAMPLE 1

Composition of the reagent: Hoechst 33342 dye, 1.00 mg/l, tetracain 200 mg/l, mannit 2000 mg/l, EGTA 0.76 mg/l, magnesium-chloride (containing 6 H₂O molecule), 0.61 mg/l, caffeine-sodium-benzoate 4000 mg/l, tri-sodium-citrate 10000 mg/l, glucose 20000 mg/l, glycerol (87%) 105 mg/l, distilled water 30 ml, RPMI 1640 culture to make 100 ml (pH=7.25; $\mu$=2.10)

EXAMPLE 2

The ingredients are essentially the same as in Example 1 but the ingredients of the culture media are also listed. The reagent thus contains the following ingredients:

| | Composition of the Reagent | pH = 7.25<br>$\mu$ = 2.10 |
|---|---|---|
| 1. | Arginine | 200.00 mg/L |
| 2. | Asparagine (H₂O) | 56.82 mg/L |
| 3. | Asparaginic acid | 20.00 mg/L |
| 4. | Biotine | 0.20 mg/L |
| 5. | Vitamin B₁₂ | 0.005 mg/L |
| 6. | Cysteine-disodium | 59.00 mg/L |
| 7. | EGTA | 0.76 mg/L |
| 8. | Phenilalanine | 15.00 mg/L |
| 9. | Phenole Red | 5.00 mg/L |
| 10. | Folicacid | 1.00 mg/L |
| 11. | Glycerol (87%) | 105.00 mg/L |
| 12. | Glucose | 22000.00 mg/L |
| 13. | Glutanic acid | 20.00 mg/L |
| 14. | Glutamine | 300.00 mg/L |
| 15. | Glutathione | 1.00 mg/L |
| 16. | Glycine | 10.00 mg/L |
| 17. | Histidine | 15.00 mg/L |
| 18. | Hictoxyprolyn | 20.00 mg/L |
| 19. | Hoechst 33342 | 1.00 mg/L |
| 20. | Inosite | 35.00 mg/L |
| 21. | Isoleucyn | 50.00 mg/L |
| 22. | Calciumpantotenole | 0.25 mg/L |
| 23. | Calcium-nitrate (Ca(NO₃)₂, 6*H₂O | 70.00 mg/L |
| 24. | Calcium-chloride | 400.00 mg/L |
| 25. | Caffeine-sodium-bensoate | 4000.00 mg/L |
| 26. | Cholin-chlorid | 3.00 mg/L |
| 27. | Leucine | 50.00 mg/L |
| 28. | Lysine | 40.00 mg/L |
| 29. | Magnesium-chloride 6*H₂O (5 mM) | 0.61 mg/L |
| 30. | Magnesium-sulphate (7*H₂O) | 100.00 mg/L |
| 31. | Mannite | 2000.00 mg/L |
| 32. | Methionine | 15.00 mg/L |
| 33. | NaCl | 6000.00 mg/L |
| 34. | NaHCO₃ | 2000.00 mg/L |
| 35. | Na₂HPO₄ | 800.00 mg/L |
| 36. | Nicotine-amid | 1.00 mg/L |
| 37. | Para-amino benzoic-acid | 1.00 mg/L |
| 38. | Proline | 20.00 mg/L |
| 39. | Pyridoxin | 1.00 mg/L |
| 40. | Riboflavine | 0.20 mg/L |
| 41. | Serine | 30.00 mg/L |
| 42. | Tetracaine | 200.00 mg/L |
| 43. | Thiamine | 1.00 mg/L |
| 44. | Thyrosine disodium | 25.00 mg/L |
| 45. | Threonine | 20.00 mg/L |
| 46. | Trisodium-citrate | 10000.00 mg/L |
| 47. | Trypthofhan | 5.00 mg/L |
| 48. | Valine | 20.00 mg/L |
| 49. | Distilled Water | ad 1000.00 mL |

EXAMPLE 3

3.0 milliliters of the invented reagent are added to 7.0 milliliters of a human blood sample or a maximum of 10.0 milliliters of a human body fluid sample. The sample is shaken and incubated at +4 degrees Celsius for 120 minutes. The sample is then stored for a maximum of 24 to 72 hours. Double centrifugation is then performed at +4 degrees Celsius. First, the sample is centrifuged at 800 g for 10 minutes. The supernatant can then be filtered before it is concentrated at 20,000 g for 20 minutes. A seven milliliter sample yields a concentrated precipitate of 10 microliters, of which three microliters are examined under the microscope.

EXAMPLE 4

The procedure according to the invention is executed applying the reagent of Example 1. Sample sterility is maintained and—after the removal of antibodies, blood cells and platelets and increasing the concentration of pathogenic bacteria—culturing and other conventional non-serological procedure can be performed more efficiently.

The following is a series of tables respectively shown in FIGS. 3–5. Table 1, shown in FIG. 3, lists the common human infections by spirochetes and their causative agents, Table 2, shown in FIG. 4, demonstrates the differential diagnosis of spirochetoses and Table 3, shown in FIG. 5, deals with comparative studies.

Two figures (FIGS. 1 and 2) about the causative agent and its shedding are included as attachments.

What is claimed is:

1. A reagent for microscopy-based detection of pathogens from body fluids, containing the following ingredients: 125–200 mg/l of tetracaine, 1500–2000 mg/l of mannite, 0.76–0.114 mg/l of etilene bis[exyetiline-nitrilo]-tetraacetate, about 0.60 mg/l of magnesium-chloride, 2000–4000 mg/l of caffeine-sodium-benzoate, 1800–2200 mg/l of glucose, 75–105 mg/l of glycerol, 10000 mg/l of tri-sodium-citrate, 20 to 40 ml of distilled water and a culture media.

2. The reagent according to claim 1, characterised in that the pathogens are spirochetes.

3. The reagent according to claim 1, characterised in that the ingredients further include 1.00 mg/l of dye.

4. A procedure for microscopy-based detection of pathogens from body fluids, characterised in that a given amount of the reagent according to claim 1, is added to a sample of human blood as the body fluid, the sample is shaken, incubated, the blood cells and the platelets are then separated from the sample, and the sample is concentrated and examined under a microscope to detect pathogens which may be contained therein.

5. The procedure according to claim 4, characterised in that the separation of the blood cells and platelets from the sample is carried out by sedimentation, slow centrifugation, and high-speed centrifugation.

6. The procedure according to claim 5, characterised in that it is employed in the detection of *Borrelia burgdorferi sensu lato*.

7. The procedure according to claim 4, characterized in that the sample concentration is carried out by high-speed centrifugation.

8. The procedure according to claim 7, characterised in that it is employed in the detection of *Borrelia burgdorferi sensu lato*.

9. The procedure according to claim 4, characterised in that it is employed in the detection of *Borrelia burgdorferi sensu lato*.

10. The procedure according to claim 4, characterised in that the pathogens are spirochetes.

11. The procedure according to claim 4, characterized in that the sample is stored after being incubated, and before the blood cells and the platelets are separated from the sample.

12. A method for microscopy-based detection of pathogens from body fluids, the method comprising the steps of:

mixing a given amount of reagent to a sample of blood, the reagent containing: 125–200 mg/l of tetracaine, 1500–2000 mg/l of mannite, 0.76–0.114 mg/l of etilene bis[exyetiline-nitrilo]-tetraacetate, about 0.60 mg/l of magnesium-chloride, 2000–4000 mg/l of caffeine-sodium-benzoate, 1800–2200 mg/l of glucose, 75–105 mg/l of glycerol, 10000 mg/l of tri-sodium-citrate, 20 to 40 ml of distilled water, and a culture media;

incubating the sample;

separating blood cells and platelets from the sample;

concentrating the sample; and examining the sample with a microscope to detect pathogens which may be contained therein.

13. The method according to claim 12, further comprising the step of storing the sample after performing the incubating step and before performing the separating step.

14. The method according to claim 12, wherein the reagent further contains 1.00 mg/l of dye.

15. The method according to claim 12, wherein the pathogens are spirochetes.

* * * * *